United States Patent [19]
Christmas

[11] Patent Number: 5,106,369
[45] Date of Patent: Apr. 21, 1992

[54] PERCUTANEOUS UMBILICAL CORD STABILIZER

[75] Inventor: James T. Christmas, Richmond, Va.

[73] Assignee: Board of Regents, The University of Texas System, Austin, Tex.

[21] Appl. No.: 619,190

[22] Filed: Nov. 28, 1990

[51] Int. Cl.$^5$ .............................................. A61M 5/00
[52] U.S. Cl. ....................................... 604/51; 128/20; 606/119
[58] Field of Search ................... 604/51, 52; 606/119, 606/120, 121, 122, 123, 124, 125, 126, 272, 273, 274; 128/898, 20

[56] References Cited

U.S. PATENT DOCUMENTS

| | | | |
|---|---|---|---|
| 1,708,578 | 4/1929 | Hyde | 128/20 |
| 3,630,190 | 12/1971 | Baker | 606/119 X |
| 4,935,008 | 6/1990 | Lewis, Jr. | 604/52 |

*Primary Examiner*—William H. Grieb
*Attorney, Agent, or Firm*—Arnold, White & Durkee

[57] ABSTRACT

A medical method and apparatus are provided whereby an umbilical cord can be stabilized by being held against an interior uterine wall, and whereby medical procedures can be performed on said stabilized umbilical cord. The apparatus comprises a first needle which is inserted into the uterine cavity and a wire with memory characteristics which passes through the first needle and which forms a curved hook upon being extended from the distal end of the first needle. The hook is used to cradle the umbilical cord without puncturing or otherwise traumatizing the cord, and to hold and stabilize the cord so that various medical procedures can be performed upon the cord. These procedures are performed by inserting a second needle into the uterine cavity either directly through the abdominal and uterine walls, or by passing the second needle through the lumen of the first needle. The curved wire is manipulated by means of a wire grip which is affixed to the proximal end of the wire, and which can either be permanently affixed to the wire or variably locatable upon the wire.

29 Claims, 2 Drawing Sheets

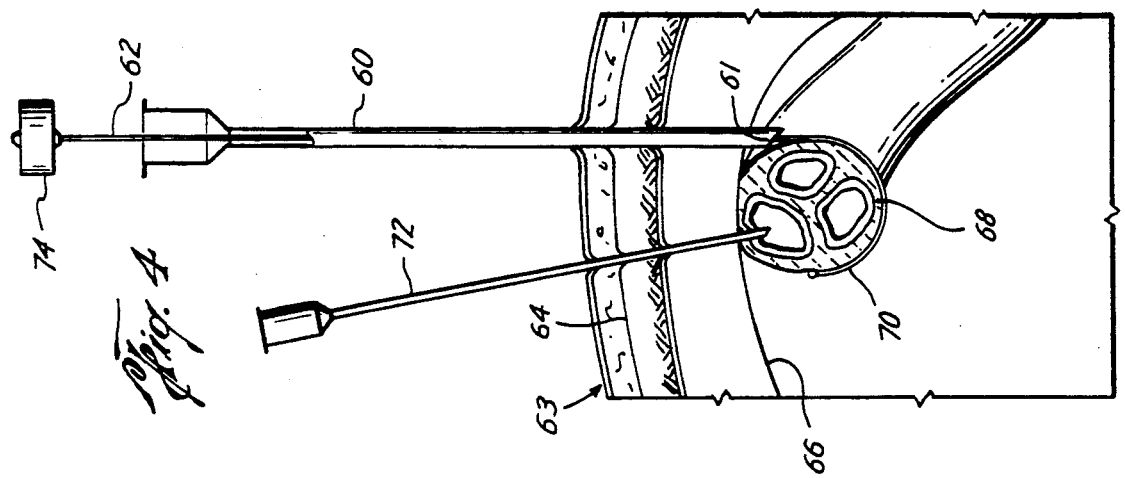
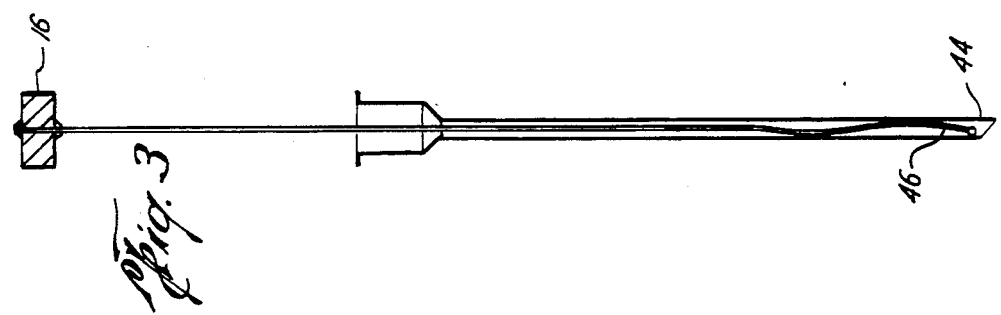
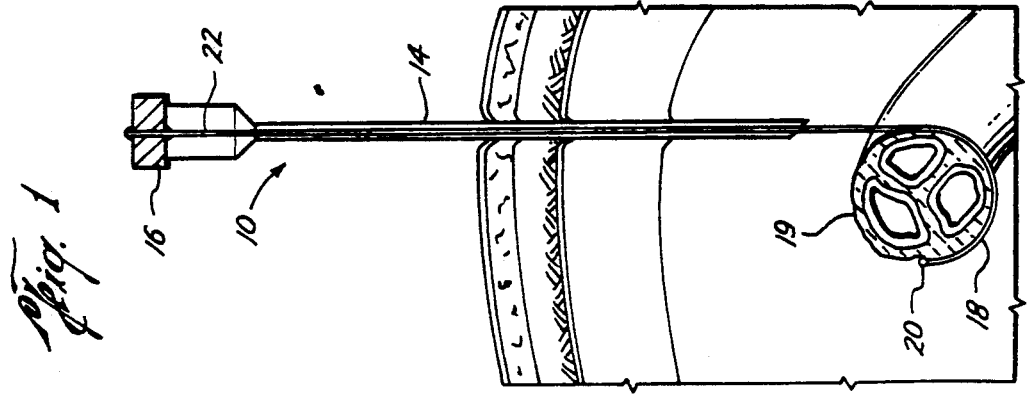

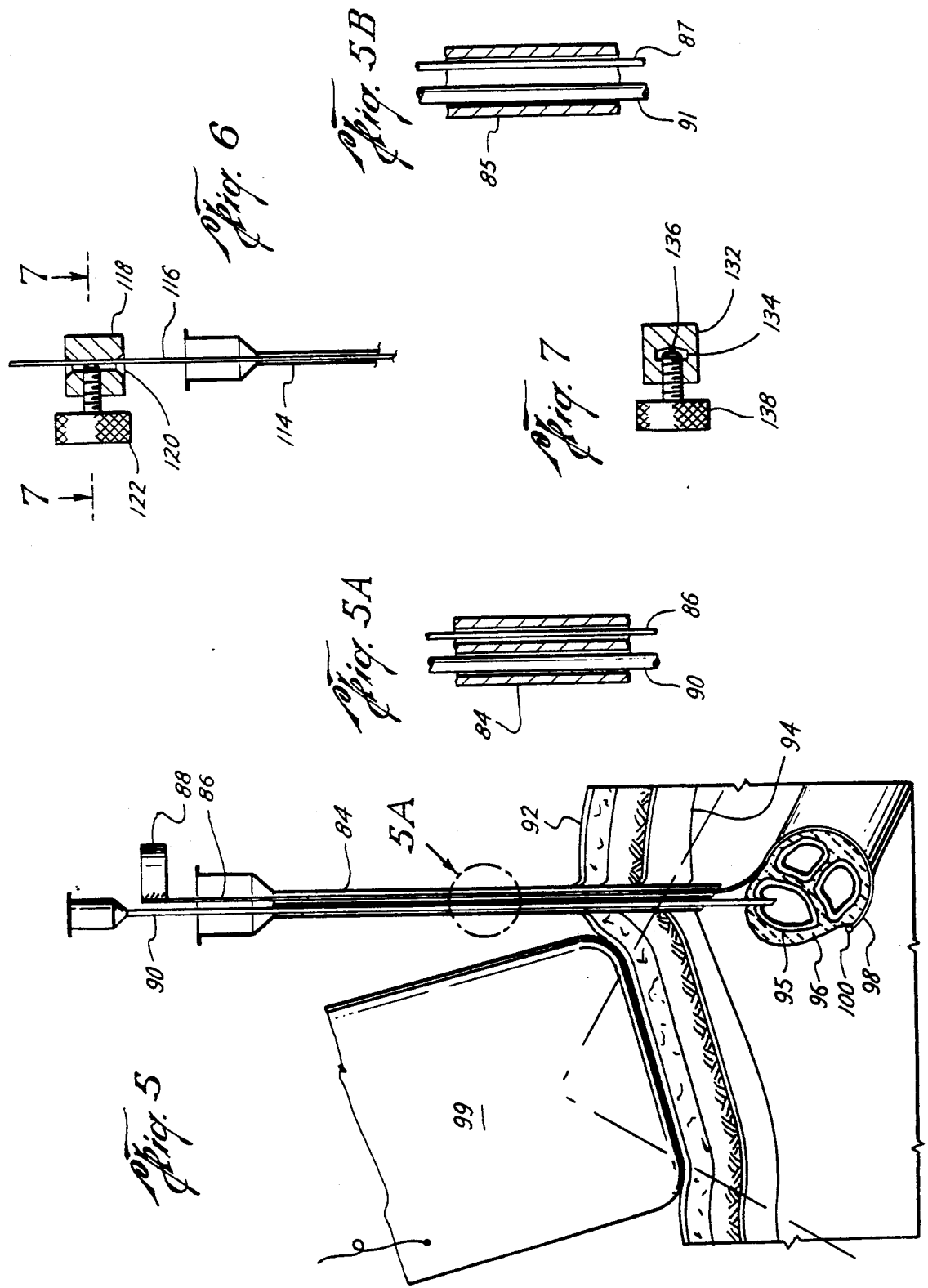

PERCUTANEOUS UMBILICAL CORD STABILIZER

BACKGROUND OF THE INVENTION

1. Field of the Invention

The present invention relates to a medical method and apparatus whereby an umbilical cord can be stabilized by being held against an interior surface of the uterine wall, and whereby medical procedures can be performed on said stabilized umbilical cord.

2. Description of the Prior Art

Percutaneous umbilical cord blood sampling has become an accepted procedure for evaluation of certain complications in high risk pregnancies. Direct fetal blood sampling has been used to evaluate fetuses with hemolytic disease of the newborn, various fetal viral infections, fetuses at risk for chromosome aberrations, as well as for evaluation of certain biochemical parameters within the fetus. In addition, percutaneous cordocentesis (puncture of the intrauterine umbilical cord with a needle) has been used extensively for intrauterine transfusion of fetuses affected with hemolytic disease of the newborn due to feto-maternal blood incompatibility.

The technique of cordocentesis involves using real-time sonography to guide a fine gauge needle into an umbilical vessel, usually the umbilical vein. In the case of an anterior placenta (i.e., placenta implanted on the anterior uterine wall), the prior art comprised passing the needle transplacentally into the placental attachment of the umbilical cord. By doing so, one could avoid trauma to the puncture site caused by fetal movement. In the case of a posteriorly implanted placenta, the prior art comprised guiding the needle through the anterior abdominal wall and amnionic cavity into the placental attachment of the umbilical cord on the posterior uterine wall. In the event that the cord insertion of a posteriorly implanted placenta could not be visualized, the site recommended for cordocentesis has been the fetal attachment of the umbilical cord. Various authors have documented inherent dangers caused by fetal movement with either of the latter two recommended procedures. Complications have ranged from inconvenience, with the needle becoming dislodged, to catastrophic, in that a rent in the umbilical vein was caused by sudden fetal movement leading to fetal exsanguination and death.

The inventor has observed cases in which there was placental complication of percutaneous cordocentesis for intrauterine transfusion in the treatment of hemolytic disease of the newborn. In one case, when an anterior placenta was traversed in an attempt to enter the transplacental attachment of the umbilical vein, a vein on the surface of the placenta was transected and a large hematoma resulted, which was noted at delivery. In another case there was a velamentous insertion of the umbilical cord (insertion of the fetal umbilical cord into the lateral margin of the placental through the membranes instead of into the central portion of the placenta). Several attempts were made to puncture the fetal umbilical vein and at one point the vein was inadvertently torn, a large hematoma developed, and the fetus subsequently expired. The hematoma was confirmed at the time of delivery. See Berkowitz, et al., *Intrauterine intravascular transfusions for severe red blood cell isoimmunization: Ultrasound-guided percutaneous approach*, Am. J. Obstet. Gynecol. 574, September 1986.

Recently, investigators have discovered that transplacental cordocentesis may actually elevate maternal antibody titers in patients with pregnancies complicated by isoimmunization. It would appear, therefore, that transplacental sampling through an anterior placenta may indeed be deleterious.

The above discussion points out the need for a method to access the umbilical vessels without traversing the placenta and without subjecting the umbilical cord to a risk of tearing due to fetal movement. This invention discloses such a method and an apparatus that is used to accomplish the method.

SUMMARY OF THE INVENTION

The present invention provides an apparatus and method to stabilize a portion of the umbilical cord within the uterus so that medical procedures can be conducted on the cord with relative safety over prior techniques used to access umbilical vessels. This invention also provides a method to stabilize the umbilical cord at a location within the uterus such that it can be accessed without puncturing the placenta and without a substantial risk of damage to the umbilical cord or dislodging of the needle tip due to fetal movement. The apparatus and method of this invention can be adapted for use on nonhuman as well as on human patients.

More specifically, the present invention provides an apparatus and method whereby a hooked wire is introduced into the uterus through a needle lumen and used to gently hook the umbilical cord and stabilize it against the uterine wall. One embodiment of this invention provides an apparatus and method to both stabilize the umbilical cord and perform percutaneous cordocentesis on the stabilized cord through a single needle penetrating the abdominal and uterine walls.

One element of this invention comprises a wire which has a blunt tip on one end and which is formed into a hook of a desired size and shape on the same end. The tip of the wire may be made blunt by any suitable method such as finishing the tip by smoothing, flattening, or polishing, or by forming a bead thereon. The hooked wire is flexible enough to be easily inserted, hook end first, through the lumen of a 20 gauge or other suitably sized needle, and to return to its original hooked shape upon extension from the distal end of the needle. This wire is long enough to allow the proximal end to be grasped and manipulated while the distal end is extended in its hooked shape from the distal end of the needle, inside of the uterus.

Another element of this invention is a wire grip assembly which allows a user of this invention to control the axial and rotational position of the distal hook end of the wire within the uterus by manual manipulation of the proximal end of the wire outside of the uterus.

This invention also provides a method of observing and controlling this apparatus through sonographic visualization techniques.

The claimed invention is summarized as a medical method and apparatus for stabilizing an umbilical cord in a desired position against the interior surface of the uterine wall, access to the interior of the uterus being obtained via a needle introduced through the abdominal and uterine walls. More particularly, the apparatus comprises a surgical spinal needle and a flexible wire, which wire can be inserted into the uterus through the needle, and which wire has a J- or C-shaped curve which re-forms when the wire is extended from the distal tip of the needle into the uterus. The exterior end of the wire is equipped with a wire grip assembly which allows the user to accurately manipulate the curved end of the wire within the uterus. The method comprises insertion of the needle of the apparatus through the uterine wall and, under ultrasonic observation, cradling the umbilical cord with the hook, pulling it to the uterine wall by withdrawing the wire concurrently with or independently of the needle, and stabilizing the cord in a desired position against the uterine wall by means of tension applied to the wire.

Once the umbilical cord is retracted and stabilized against the interior uterine wall, it is made available for the performance of any medical procedure which requires access to the umbilical cord or the fetal circulatory system. Such procedures include administration of a neuromuscular blocking agent and performance of intrauterine transfusion. This invention includes the performance of any medical procedure on the stabilized portion of the umbilical cord while using any embodiment of the invention.

When the medical procedure conducted upon the umbilical cord is complete, the umbilical cord is released from the hook of the apparatus by retracting the wire through the needle by increased tension applied to the proximal end of the wire such that the distal end of the wire is withdrawn from around the umbilical cord within the uterus and into the needle. The entire wire can then be pulled out of the needle, and the needle can be removed from the patient's body. Alternatively, the hooked end of the wire can be inserted farther into the uterus and turned away to release the umbilical cord prior to being retracted into the needle and removed from the patient.

The claimed invention will significantly reduce the risk associated with procedures which require access to the fetal circulatory system by allowing the user to puncture the uterus at any desired accessible location, and to stabilize a free portion of the umbilical cord at such location, avoiding the risks associated with penetration of the placenta and movement of the fetus.

In a preferred form, the invention utilizes a J-shaped wire hook that cradles the umbilical cord against the uterine wall so that a second needle can be inserted adjacent thereto into the umbilical cord for the medical procedure to be performed. The procedure may be performed under sonographic visualization which is used to locate a free loop of umbilical cord within the uterus, to observe the placement of the needle and hook of the invention and to determine the positions of the umbilical vessels within the stabilized portion of the cord.

In another preferred embodiment of the invention, a C-shaped wire hook is used which holds the umbilical cord in a position, relative to the needle through which said wire passes, such that a second, smaller needle can be inserted through the first needle lumen and into the umbilical cord for injection or withdrawal of fluid. The first needle may be single-lumen or double-lumen. This embodiment may also be performed under sonographic visualization.

This invention is a novel solution to a long un-met need for a method to perform percutaneous cordocentesis on a central, free floating portion of the umbilical cord, in order to avoid problems associated with performance of the procedure near the ends of the umbilical cord.

BRIEF DESCRIPTION OF THE DRAWINGS

So that the manner in which the above-recited advantages and features of the present invention, as well as others which will be come apparent, are attained and can be understood in detail, more particular description of the invention summarized above may be had by reference to the embodiment thereof which is illustrated in the appended drawings, which drawings form a part of this specification.

It is to be noted, however, that the appended drawings illustrate only typical embodiments of the invention and are therefore not to be considered limiting of its scope, for the invention may admit to other equally effective embodiments.

FIG. 1 is a sectional view of a preferred embodiment of percutaneous umbilical cord stabilizer according to the present invention, showing a J-shaped wire hook extended from the distal end of the needle;

FIG. 2 is a sectional view of an alternate preferred embodiment of the same invention with a C-shaped wire hook rather than the J-shaped wire hook of FIG. 1;

FIG. 3 is a sectional view of the invention with the hooked wire withdrawn inside of the needle, positioned for insertion into the uterus or withdrawal from the uterus;

FIG. 4 is a sectional view of the embodiment of FIG. 1, shown as it is used to stabilize an umbilical cord against the uterine wall. In this figure a second needle is shown penetrating the uterine wall to perform a percutaneous cordocentesis on the stabilized umbilical cord.

FIG. 5 shows the embodiment of FIG. 2 as it is used to stabilize an umbilical cord against the uterine wall, while a second needle is inserted through the second lumen of the first needle to perform a percutaneous cordocentesis. Note that stabilization and cordocentesis are both performed through a single puncture of the uterine wall;

FIGS. 5A and 5B illustrate the passage of the wire and the second needle through a double-lumen needle and a singlelumen needle, respectively.

FIG. 6 is a perspective view of the wire grip assembly which is part of this invention; and FIG. 7 is an elevational view of the end of the wire grip assembly.

DESCRIPTION OF THE PREFERRED EMBODIMENTS

Referring to FIG. 1, a preferred embodiment of the percutaneous umbilical cord stabilizer 10 comprises a surgical needle 14 of an appropriate size to slidably receive a flexible steel wire with memory characteristics 22 shaped into a hook at the distal end 18 and equipped with a blunt bead tip 20. The proximal end of the wire 22 is equipped with a wire grip 16 which provides a means for manipulating the wire 22 to accurately control the position of the hook 18. Referring to FIG. 3, the wire 46 is constructed of a material which is adequately flexible to be withdrawn completely inside the needle 44 and which will return its original hooked shape when extended from the needle as shown in FIG. 1 and FIG. 2.

FIG. 2 shows another preferred embodiment of this invention wherein the wire is constructed to form a hook of a different shape at the distal end 32. The shape shown in FIG. 1 is referred to in the claims as a J-shaped hook 18 and the shape shown in FIG. 2 is referred to in the claims as a C-shaped hook 32. The hook is of a size and shape which will allow the user to gently hook and cradle an umbilical cord within the uterus, and it is anticipated that wires with hooks of several shapes and sizes will be available for selection depending upon the gestational age of the fetus and the procedure to be performed.

Referring to FIGS. 1 and 2, the end of the wire which is formed into a hook 18, 32 is tipped with a blunt bead 20, 34 to avoid puncturing the umbilical cord 19 during efforts to engage the cord within the hook. The tip of the wire may be made blunt by any suitable method, such as finishing the tip by smoothing, flattening or polishing, by making the tip very flexible, or by forming a bead upon the tip of the wire.

The wire may be manufactured from any suitable material, including various plastics and metal alloys. This material must be suitable for surgical use, and must have appropriate memory characteristics to enable it to be extended through a needle and to reform its original shape upon extension from the needle. Suitable materials include Raychem Corp. Alloy BB.

The method claimed by the invention may be performed under sonographic visualization. In such an application, as shown in FIG. 5, a sonographic transducer 99 is manipulated on the abdominal wall 92 overlying the uterus to determine the location of the placenta and a free floating loop of the umbilical cord 96. A location is chosen for insertion of the percutaneous umbilical cord stabilizer needle 84, and such insertion is performed. Sonographic visualization is then again used to observe the extension of the hooked end of the wire 98 from the needle inside of the uterus, and also to observe the cradling of the umbilical cord 96 within the hooked end of the wire. The hooked end of the wire 98 is intended to wrap around the umbilical cord 96, and the tip of the wire 100 is blunt to avoid puncturing or otherwise traumatizing the cord. Once the umbilical cord is retracted and stabilized against the uterine wall 94, sonographic methods can again be used to locate the vessel 95 within the stabilized portion of the umbilical cord upon which percutaneous cordocentesis is to be performed.

FIG. 4 shows how the embodiment shown in FIG. 1 is used. The wire 62 is retracted into the needle 60 by use of the wire grip 74, as shown in FIG. 3. The needle is then inserted through the skin 63 and the abdominal and uterine walls 64, 66 under sonographic visualization. The wire hook 70 is then extended from the needle 60 to return to its hook shape 70. The needle and hook are used to engage a free floating portion of the umbilical cord 68 within the hook structure by manual manipulation of the exterior end of the needle 60 and the wire grip 74, and to draw the cord against the uterine wall 66 into a stable position as shown in FIG. 4. FIG. 4 also shows a second needle 72 inserted through the abdomen and into the umbilical cord, performing a percutaneous cordocentesis on the stabilized cord.

At the termination of the procedure, after any needle 72 used to puncture the umbilical cord has been removed, the wire hook 70 is withdrawn into the needle 60 by applying tension to the wire 62 by means of the wire grip 74. The wire hook 70 is flexible enough such that when additional tension is applied to the proximal end of the wire 62 the hook end 70 can be drawn around the umbilical cord 68 without damage to the cord. Alternatively, the hook can be further extended from the distal end of the needle 61, and rotated to release the umbilical cord. The hook is then withdrawn into the needle 60, as shown in FIG. 3, and the needle is withdrawn from the patient's body.

The preferred embodiment shown in FIG. 2, having a C-shaped hook, is used as shown in FIG. 5 to stabilize the umbilical cord 96 against the uterine wall 94 by the use of a C-shaped hook 98. The first needle 84 is a double lumen needle. The wire having a C-shaped hook passes through one lumen and holds the umbilical cord in a manner which allows a second needle 90 to be inserted through the second lumen of the first needle 84 and into the umbilical cord 96 without requiring a second puncture of the abdominal and uterine walls 92, 94. The methods of insertion and removal of the apparatus shown in FIG. 5 are otherwise identical to those described in conjunction with the embodiment shown in FIG. 4. All procedures and methods described in this application may be performed under sonographic visualization.

The single puncture method illustrated in FIG. 5 can be performed through either a single lumen needle or a double lumen needle. FIGS. 5 and 5A show the use of a double lumen needle 84, where the wire 86 passes through one lumen and the second needle 90 passes through the other lumen. FIG. 5B shows the alternative use of a single lumen needle 85, wherein both the wire 87 and the second needle 91 pass through the single lumen.

Regardless of the embodiment of the apparatus which is used, be it one of the embodiments described above or another, once the umbilical cord is stabilized against the uterine wall and percutaneous cordocentisis is preformed on the cord so stabilized, any medical procedure requiring access to the fluids of the umbilical cord can be preformed. Such procedures include removal of fluid or tissue samples, administration of a neuromuscular blocking agent and performance of an intrauterine transfusion.

FIG. 6 shows a preferred embodiment of the wire grip. This is a device which is clamped to the proximal end of the wire 116 which extends into the needle 114. The grip is equipped with a thumb screw 122 by which the user can clamp the wire grip onto the wire 116 at any desired axial and radial position relative to the hook structure at the distal end of the wire. After noting the relative longitudinal position and radial orientation of the grip with respect to the hook, the user can accurately control the position of the hook inside of the uterus by manipulating the wire grip 118. A preferred embodiment of the wire grip, as shown in FIG. 6, comprises a wire grip body 118 having a channel 120 through which the wire 116 can pass. The wire 116 is securely held within the wire grip by compression of the wire between the wall of the channel 120 and a screw 122. The channel may be of any size and shape that allows the wire to be securely held by the screw.

FIG. 7 shows an elevational view of the end of the wire grip showing the channel 134 through the body 132 and the screw 138 being used to securely retain the wire 136 within the wire grip assembly. The wire grip assembly allows the user to conveniently extend, retract and rotate the wire during the course of the procedures described above.

Alternatively, a wire grip of suitable size and shape can be manufactured permanently at a fixed position on the wire by soldering, brazing, welding, gluing, or other suitable method. This alternative is illustrated in FIGS. 1–5, which show wire grips 16, 74, 88 soldered or otherwise affixed to the proximal end of the wire.

Further modifications and alternative embodiments of the apparatus and method of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the shape, size and arrangement of parts. For example, equivalent elements or materials may be substituted for those illustrated and described herein, parts may be reversed, and certain features of the invention may be utilized independently of the use of other features, all as would be apparent to one skilled in the art after having the benefit of this description of the invention.

What is claimed is:

1. Apparatus for stabilizing an umbilical cord in a uterine cavity, comprising:
    a needle adapted for insertion into the uterine cavity;
    a blunt-tipped wire slidable through the needle lumen, of length to extend into the uterine cavity and exterior of the needle, the wire having a memory curved end, the curved end adapted to partially encircle an umbilical cord within the uterine cavity.

2. Apparatus of claim 1 wherein the curved end of the wire is J-shaped.

3. Apparatus of claim 1 wherein the curved end of the wire is C-shaped.

4. Apparatus of claim 1 wherein the blunt tip of the wire is formed of a bead.

5. Apparatus of claim 1 further comprising a wire grip located on a portion of the wire exterior to the proximal end of the needle, opposite the curved end of the wire.

6. Apparatus of claim 5 wherein the wire grip comprises a clamp slidable along the wire to grip the wire at a desired position.

7. Apparatus for performing percutaneous cordocentesis comprising:
    a first needle adapted for insertion into a uterine cavity;
    a blunt-tipped wire slidable through the first needle lumen, of length to extend into the uterine cavity and exterior of the first needle, the wire having a memory curved end, the curved end adapted to partially encircle an umbilical cord within the uterine cavity; and
    a second needle slidable through the first needle lumen adjacent the wire.

8. Apparatus for performing percutaneous cordocentesis comprising:
    a first needle, having two lumens, adapted for insertion into a uterine cavity;
    a blunt-tipped wire slidable through one of the lumens of the first needle, of length to extend into the uterine cavity and exterior of the first needle, the wire having a memory curved end, the curved end adapted to partially encircle an umbilical cord within the uterine cavity; and
    a second needle slidable through the second lumen of the first needle.

9. Apparatus of claim 7 or 8 wherein the curved end of the wire is C-shaped.

10. Apparatus of claim 7 or 8 further comprising a wire grip located on a portion of the wire exterior to the proximal end of the needle, opposite the curved end of the wire.

11. Apparatus of claim 10 wherein the wire grip comprises a clamp slidable along the wire to grip the wire at a desired position.

12. A method of stabilizing an umbilical cord, comprising the steps of:
    inserting a needle into the uterine cavity;
    extending a wire through the needle, the wire having a memory curve and a blunt tip on the distal end such that the memory curve forms a hook inside of the uterus when the distal end of the wire is extended from the needle;
    locating the umbilical cord and cradling it within the curved hook formed by the wire.

13. The method of claim 12 further comprising the step of retracting the apparatus sufficiently to stabilize the umbilical cord against the uterine wall.

14. The method of claim 12 wherein the steps are performed under sonographic visualization.

15. The method of claim 13 wherein the steps are performed under sonographic visualization.

16. A method of performing percutaneous cordocentesis, comprising the steps of:
    inserting a first needle into the uterine cavity;
    extending a wire through the first needle, the wire having a memory curve and a blunt tip on the distal end such that the memory curve forms a hook inside of the uterus when the distal end of the wire is extended from the first needle; and
    locating the umbilical cord and cradling it within the curved hook formed by the wire.
    inserting a second needle into the umbilical cord.

17. The method of claim 16 further comprising the step of retracting the first needle and wire to stabilize the umbilical cord against the uterine wall prior to insertion of the second needle.

18. The method of claim 16 wherein the steps are performed under sonographic visualization.

19. The method of claim 17 wherein the steps are performed under sonographic visualization.

20. The method of claim 16 wherein the curved end of the wire is C-shaped.

21. The method of claim 20 wherein the second needle passes through the lumen of the first needle to access the umbilical cord.

22. The method of claim 16 further comprising the step of administering a neuromuscular blocking agent into an umbilical vessel through the second needle.

23. A method of performing intrauterine transfusion comprising the steps of:
    inserting a first needle into the uterine cavity;
    extending a wire through the first needle, the wire having a memory curve and a blunt tip on the distal end such that the memory curve forms a hook inside of the uterus when the distal end of the wire is extended from the needle;
    locating the umbilical cord and cradling it within the curved hook formed by the wire;
    inserting a second needle into the umbilical cord; and
    transfusing fluids through the second needle into or out of the umbilical cord.

24. The method of claim 23 further comprising the step of administering a neuromuscular blocking agent into an umbilical vessel through the second needle.

25. The method of claim 23 further comprising the step of retracting the apparatus to maintain the umbilical cord against the uterine wall prior to the insertion of the second needle.

26. The method of claim 23 wherein the steps are performed under sonographic visualization.

27. The method of claim 25 wherein the steps are performed under sonographic visualization.

28. The method of claim 23 wherein the curved end of the wire is C-shaped.

29. The method of claim 28 wherein the second needle passes through the lumen of the first needle to access the umbilical cord.

* * * * *